United States Patent [19]

Kelleher et al.

[11] Patent Number: 4,673,633

[45] Date of Patent: Jun. 16, 1987

[54] METHOD OF DETERMINING CYSTIC FIBROSIS CILIOSTATIC FACTOR

[75] Inventors: Thomas J. Kelleher, Springlake Heights; Paul T. Nix, Jackson, both of N.J.

[73] Assignee: CooperBiomedical, Inc., Malvern, Pa.

[21] Appl. No.: 625,600

[22] Filed: Jun. 28, 1984

[51] Int. Cl.$^4$ ............................ G01N 1/00; G01N 1/40
[52] U.S. Cl. ............................................. 435/4; 435/22; 435/102; 435/184; 435/810
[58] Field of Search .................... 435/4, 18, 21, 22, 14, 435/98, 99, 102, 184, 210, 810; 536/103

[56] References Cited

U.S. PATENT DOCUMENTS 4,355,110  5/1981  Line et al. ............................ 435/210

OTHER PUBLICATIONS

Gillard et al., "Cystic Fibrosis: Enzymatic Detection of a Ciliostatic Factor", *Pediat. Res.* 10: 907-910 (1976).
Bender et al., *Methods in Enzymology*, vol. 8, (1966) pp. 555-559.
Gillard et al., "Biochemistry", vol. 16, No. 18, (1977) pp. 3978-3987.
Stryer, *Biochemistry, 2nd Ed. (1981) W. H. Freeman and Co., San Francisco, pp. 357-362 and 376-377.*
Nelson et al., Cystic Fibrosis Club Abstract, 25th Annual Meeting, San Jose, Calif., Apr. 30, 1984.
Impero et al., "Pediatr. Res." vol. 15, (1981), pp. 940-944.

*Primary Examiner*—Sidney Marantz
*Attorney, Agent, or Firm*—Vorys, Sater, Seymour & Pease

[57] ABSTRACT

A method for detecting the presence of cystic fibrosis ciliostatic factor in mammalian body fluid comprises contacting an enzyme whose activity is inhibited by the factor with a substrate for the enzyme in the presence of the body fluid, the substrate being substantially resistant to reactions catalyzed by enzymes in the body fluid, whereby the substrate is converted by the enzyme at a measurable rate, and
comparing the rate of substrate conversion with the rate of substrate conversion by the enzyme in the absence of cystic fibrosis ciliostatic factor.

20 Claims, No Drawings

METHOD OF DETERMINING CYSTIC FIBROSIS CILIOSTATIC FACTOR

BACKGROUND OF THE INVENTION

1. Field of the Invention

This invention relates to methods for diagnosing cystic fibrosis in patients afflicted with that disease and more particularly to methods for diagnosing cystic fibrosis by detecting cystic fibrosis ciliostatic factor in body fluids of patients and carriers

2. Description of the Prior Art

Cystic fibrosis (CF) is a debilitating genetic disease characterized by abnormalities of secretory organs in the body The disease is the most common lethal genetic disease of Caucasian children, and those individuals who are diagnosed as having CF usually die before the age of twenty-five. The basic genetic defect and its mode of operation are unknown, but the defective gene is relatively common in the Causasian population, about 5% of the populace being heterozygous carriers. Since the inheritance follows the typical autosomal recessive pattern, CF homozygotes express the gene and exhibit symptoms of the disease, while CF heterozygotes are carriers of the gene but do not have symptoms of the disease.

Because the disease is life-threatening, therapy is essential. Accordingly, an accurate and reliable method of diagnosis is very important. However, the clinical picture of the disease is highly variable and clinical findings alone cannot be relied on for diagnosis. A summary of various biochemical tests for CF is found in Heeley, A. F., et al, Clin. Chem. 29, 2011-2018 (1983). The most frequently used method for CF diagnosis at present is the "sweat test", in which CF homozygotes show increased concentration of NaCl in their sweat caused by mal-reabsorption of salt. At present, there is no test for CF heterozygotes.

Other biochemical tests for CF have been based on the finding that the body fluids (blood, urine, saliva, etc.) of CF positive individuals have been found to contain abnormal substances. One of such substances which has been found to be a useful marker for cystic fibrosis is ciliostatic factor.

This substance has been given the name cystic fibrosis ciliostatic factor because it possesses the characteristic biological property of inhibiting the motion of actively moving cilia. This property is the basis of several different ciliary bioassays which have been developed to detect CF by observing the ciliostatic effect of body fluids containing CF ciliostatic factor on oyster gill cilia, mussels cilia, rabbit tracheal cilia and a number of other cilia systems. Although these bioassays are not very precise and certainly not quantitative, they can identify individuals having CF. However, because the technique is slow and difficult and requires highly trained personnel, the assays using ciliated cell systems have not been useful in a clinical setting.

Because of the difficulty of ciliated cell assays, other assays for CF ciliostatic factor have been sought. Since it was known that certain compounds which have ciliostatic activity, e.g., polyhydroxyamines, are also inhibitors of mammalian debranching enzyme, an enzyme important for breakdown of glycogen in humans, the effect of CF ciliostatic factor on this enzyme was investigated. It was found that CF ciliostatic factor is, indeed, an inhibitor of mammalian debranching enzyme, and an assay has been developed using the enzyme inhibition properties of this factor using glycogen phosphorylase limit dextrin as a substrate (Gillard, B. K., et al, J. Pediatric Res. 10, 907-910 (1976)).

An additional advantage of the inhibition assay procedure is that it appears to be able to distinguish not only homozygote CF patients from normal individuals, but also identify and distinguish heterozygote CF carriers from homozygote CF patients. However, the assay as described in the literature suffers from several deficiencies; (a) laborious sample processing must be used to rid the specimen of alpha-amylase, (b) none of the assay components are readily available from commercial sources, (c) no large scale clinical evaluation of the procedure has been carried out. The removal of alpha-amylase from the sample is necessary because the substrate used in the literature assay is also acted on by alpha-amylase. Furthermore, the purification is especially laborious because CF ciliostatic factor is bound to alpha-amylase in the body fluid (although it does not inhibit the alpha-amylase). In view of these problems, the method is not acceptable as a clinical diagnostic tool for CF. Indeed, hitherto there has been no clinically useful and practical technique for the detection of CF ciliostatic factor.

Hence a need has continued to exist for a biochemical method for analyzing for CF ciliostatic factor which is useful in clinical diagnosis of CF.

SUMMARY OF THE INVENTION

Accordingly, it is an object of the invention to provide a biochemical method for detecting cystic fibrosis.

A further object is to provide a biochemical method for detecting CF ciliostatic factor.

A further object is to provide a method for detecting CF ciliostatic factor in body fluids of patients having CF.

A further object is to provide a method for detecting CF ciliostatic factor in body fluids without preliminary purification of the body fluid sample.

A further object is to provide a method for detecting CF ciliostatic factor in body fluids of carriers of the CF gene.

A further object is to provide a biochemical method for detecting CF ciliostatic factor based on enzyme inhibition.

Further objects of the invention will become apparent from the description of the invention which follows.

The objects of the invention are achieved by a method for detecting the presence of cystic fibrosis ciliostatic factor in mammalian body fluid comprising contacting an enzyme whose activity is inhibited by the factor with a substrate for the enzyme in the presence of the body fluid, the substrate being substantially resistant to reactions catalyzed by enzymes in the body fluid, whereby the substrate is converted by the enzyme at a measurable rate, and comparing the rate of substrate conversion with the rate of substrate conversion by the enzyme in the absence of cystic fibrosis ciliostatic factor.

DETAILED DESCRIPTION OF THE INVENTION AND PREFERRED EMBODIMENTS

The enzyme used in the process of this invention must be an enzyme whose activity is inhibited by contact with CF ciliostatic factor. Any type of enzyme can be used, e. g., a protease, lipase, amylase or the like. Inhibition of the enzyme activity is usually detected by monitoring the rate of conversion of a substrate and comparing the rate with the rate of the enzyme in the absence of inhibitor. Any method of monitoring the rate of the enzyme-catalyzed reaction is suitable; however, the rate is usually followed by monitoring the rate of formation of the product of the enzyme-catalyzed reaction.

Because of the well developed tests for monosaccharides such as glucose, it is preferred that the enzyme be an enzyme which catalyzes the hydrolysis of a polysaccharide carbohydrate substrate. The reaction product of the enzymatic action will then be an oligosaccharide or a monosaccharide which can be readily detected by methods known to those skilled in the art, and the rate of the enzyme-catalyzed reaction can be easily followed by monitoring the rate of formation of the product.

Enzymes such as mammalian debranching enzyme and pullulanase fulfill these criteria. The mechanism by which CF ciliostatic factor inhibits these enzymes is not known, but the inhibition is noncompetitive with respect to the polysaccharide.

Mammalian debranching enzyme has been isolated from rabbit muscle and has been shown to be a single polypeptide chain which possesses three different primary binding sites and two different catalytic sites. Its enzyme activity may be described as amylo-1,6-glucosidase/4-glucanotransferase. The usual substrate of the enzyme activity which is inhibited by CF ciliostatic factor is partially degraded glycogen, a branched polysaccharide, after several sugar residues in the branch have been removed by the transferase activity leaving only a single glucose residue attached to the main polymer chain. The preparation and isolation of mammalian debranching enzyme are described in Watts, T. E., et al., Analytical Biochem. 49, 479 (1972).

Another suitable enzyme which the inventors have discovered to be inhibited by contact with CF ciliostatic factor is pullulanase. Pullulanase is a commercially available bacterial limit dextrinase (poly 1-6 maltotriose hydrolase) from *Enterobacter aerogenes* which degrades pullulan (poly 1-6 maltotriose) exclusively into maltotriose units. This enzyme is a glucanase with no transferase or glucosidase activities such as found in mammalian debranching enzymes (Bender, H., et al., Methods in Enzymology, Vol 8, 555–559 (1966)).

The substrate for the enzyme inhibited by CF ciliostatic factor must be inert to the action of enzymes present in the body fluids used in the assay. This property is necessary, since if the substrate were to be acted on by such enzymes, the reaction products produced by these other enzymes would be indistinguishable from the reaction products produced by the enzyme inhibitable by CF ciliostatic factor. Evidently, under these circumstances the action of these other enzymes would interfere with the enzyme inhibition assay of the invention.

A preferred substrate for use in the assay of this invention is pullulan. Pullulan is a cell wall glucan from the fungus *Aureobasidium pullulans* which is composed of poly 1-6 maltotriose units. Since the linkage between the maltotriose units is 1-6, some similarity exists between the branch points of pullulan and those of starch. The novel property of pullulan utilized by this invention is the fact that pullulan is not degraded by human amylases present in crude human body fluids such as serum, saliva and urine. Therefore it is a particularly useful substrate for a carbohydrate-based diagnostic test for cystic fibrosis using crude human body fluids.

Since the linkages between the three glucose residues in maltotriose are 1-4, while the linkages between the maltotriose residues in pullulan are 1-6, pullulanase degrades pullulan to maltotriose units, but no further. In order to detect the presence of maltotriose units it is convenient to hydrolyze the maltotriose further into its glucose constituents by contact with an alpha-glucosidase such as maltase. The glucose produced by this hydrolysis may then be detected by conventional spectrophotometric analysis for glucose based on the glucose/peroxidase reaction (absorbance at 500 nm) (Trinder, P., Ann. Clin. Biochem. 6, 24 (1969)) or on the hexokinase/glucose-6-phosphate dehydrogenase reaction (absorbance at 340 nm) (Bondar, R. J. L., et al., Clin. Chem. 20, 586(1974)). These methods for detecting and quantitating the amount of glucose present are well known to those skilled in the art, and reagents for carrying out the reaction are commercially available, for example, from CooperBiomedical, Inc., Malvern, Pa.

Another substrate is maltodextrin phosphorylase limit dextrin which is the product of the action of maltodextrin phosphorylase on maltodextrin, as disclosed in Nix et al., U.S. Pat. No. 4,304,854. This limit dextrin is industrially produced and is commercially available. This substrate, however, is degraded by the amylases present in mammalian body fluids such as saliva, and accordingly, when this substrate is used, the body fluid must be at least partially purified in order to remove amylases and any contaminating sugars.

The maltodextrin phosphorylase limit dextrin may be further digested with an alpha-amylase to prepare an alpha-amylase digest of the maltodextrin phosphorylase limit dextrin which is resistant to the action of amylases and forms a good substrate for use in the test of this invention. This alpha-amylase digest product has the main polysaccharide chains cleaved and hydrolyzed to a molecule comprising three anhydroglucose units bonded by 1-4 linkages having a short branch (two 1-4 bonded anhydroglucose units) bonded 1-6 to the central anhydroglucose unit of the main chain. The digest may be purified of monosaccharides by conventional means such as dialysis to yield an amylase-resistant substrate suitable for use in the test of this invention. This substrate accordingly has the molecular formula

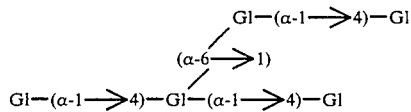

wherein G1 signifies an anhydroglucose residue and the numbers in parentheses indicate the locations of the bonds between the residues.

Alpha-amylase limit digests of any branched polysaccharide are in general amylase-resistant and are suitable substrates for use in the test of this invention.

The degree of enzyme inhibition produced by the CF ciliostatic factor is determined by comparing the rate of substrate conversion in the presence of the factor with that when the factor is absent, e. g., when body fluids from normal individuals are assayed. The method used to detect and quantitate the products of the enzymatic conversion reaction will depend on the particular enzyme/substrate combination used in the assay.

In carrying out the preferred process of this invention using mammalian debranching enzyme or pullulanase, an excess amount of the substrate for the inhibitable enzyme is dissolved in an aqueous solution buffered to a suitable pH, e.g., a pH of 5.3 to 7.1. A suitable buffer, having a pH of 6.6, is a solution of 5.9 grams of maleic acid and 1.9 mg of tetrasodium ethylenediaminetetra-acetic acid (EDTA) in 100 ml of water. Alternatively a conventional 0.03 M phosphate buffer having a pH of 6.6 may be used. The substrate solution is then mixed with a solution of a glucose-detecting reagent, e.g., a reagent based on the glucose oxidase reaction or on the hexokinase reaction as described above.

An aqueous solution of the inhibitable enzyme, e.g., pullulanase or mammalian debranching enzyme, is prepared containing 1-50 milliunits of the enzyme. If the preferred substrate pullulan is used, the enzyme solution should also contain 0.56 to 22 units of maltase. Aliquots of the enzyme solution are then mixed with measured volumes, preferably equal volumes, of the body fluids to be tested and incubated for a time to produce maximum inhibition of the enzyme by the CF ciliostatic factor in the body fluids. The reaction between the enzyme and the substrate is then initiated by mixing the enzyme/body fluid mixture with the substrate/glucose reagent mixture. The reaction is allowed to proceed at an appropriate temperature, e.g., about 30° C., for a period of time necessary to develop a distinctive absorbance in the solution. Depending on the concentration of the reagents, this may be from 3 to 30 minutes. Naturally, it is preferred to adjust the concentration of reagents so that a significant optical absorbance change occurs for the uninhibited samples (normals) in a relatively short period of time, e.g., 3-12 minutes.

By adjustment of the concentrations of the inhibitable enzyme and of the maltase, it is possible to obtain a substantial development of optical absorbance in the uninhibited samples (no CF ciliostatic factor present) in a period of 3-6 minutes while no substantial absorption occurs for the samples containing CF ciliostatic factor for a period of 12-15 minutes or more. Such a test provides a decisive criterion for the presence of CF ciliostatic factor.

It is also according to the invention to prepare a kit containing the test reagents for conducting the assay of the invention. Such a kit may comprise a first container containing the enzyme inhibitable by CF ciliostatic factor and a second container containing the substrate for the enzyme. The reagents may be present in the contaniners in lyophilized form. In performing the assay of the invention using the kit, the body fluid is added to the container containing the enzyme and the mixture is incubated for a period of time to allow the enzyme to become inhibited by contact with any ciliostatic factor which may be present in the sample of body fluid. The enzyme-body fluid mixture is then added to the second container containing the substrate for the enzyme and a further incubation is carried out for a suitable period of time, e.g., 3-12 minutes. The solution in the second container is then inspected for formation of color, or the optical absorbance is quantitatively measured with a spectrophotometer. In a preferred embodiment of the kit, the first container may contain an enzyme which catalyzes the hydrolysis of a polysaccharide substrate, such as pullulanase, and maltase; while the second container may contain a preferred substrate for the enzyme, e.g., pullulan. The kit may also contain additional containers containing reagents useful in the performance of control tests. For example an additional container may contain a positive control reagent such as maltose, and an additional container may contain a negative control reagent such as nojirimycin or 1-deoxynojirimycin, to perform the control tests as explained below in Example 1.

The invention will now be further illustrated by the following examples which are included for purposes of illustration and are not intended to limit the scope of the invention.

EXAMPLE 1

This example illustrates the inhibition of pullulanase by CF ciliostatic factor using pullulan as a substrate for the enzyme.

A pullulan substrate solution is prepared by dissolving an excess amount, e.g., 2000 mg, of pullulan in a 0.03 M phosphate buffer having a pH of about 6.6. The pullulan substrate solution is then mixed in an appropriate ratio, e.g., 1:3, with a glucose determining reagent based on the glucose oxidase reaction (Worthington Statzyme TM Glucose (500 nm) obtainable from CooperBiomedical, Inc., Malvern, Pa.).

An aqueous solution containing 68 units of maltase (alphaglucosidase) per milliliter and 1.5 units of pullulanase per milliliter is prepared. An aliquot containing 45 microliters of the enzyme solution is then combined with 45 microliters of the body fluid to be tested. The reaction is then initiated by addition of 250 microliters of the pullulan/glucose reagent mixture to give a total reaction volume of 340 microliters. The reaction is allowed to proceed at a temperature of 30° C. for 3-12 minutes while the optical absorbance of the reaction solution is followed at a wavelength of 500 nm.

The samples containing CF ciliostatic factor (from patients having CF) exhibit very little color formation during the 3-12 minute observation while samples containing body fluids from normal individuals develop substantial absorbance at 500 nm.

A confirmatory control for false positives in this test (thought to be due to antibiotics and/or ascorbic acid in the body fluid which prevent the color formation of the glucose reagent) is performed by substituting maltose for pullulan in the reagent. These controls will continue to exhibit a depressed color formation for normal individuals having a false positive test while the samples containing CF ciliostatic factor (but no antibiotic or ascorbic acid) will exhibit color formation.

A control for false negative tests is performed by adding to the enzyme preparation an inhibitor for the inhibitable enzyme (pullulanase) and/or for the maltase. A suitable inhibitor is 1-deoxynojirimycin. The false negative test develops color, usually due to glucose in the body fluid sample as a result of diabetes. In the control test, the normal non-diabetic body fluid does not produce color because no glucose is formed by the inhibited enzyme; while the diabetic body fluid produces color because of the glucose which is originally present in the body fluid.

EXAMPLE 2

This example illustrates the inhibition of mammalian debranching enzyme by CF ciliostatic factor using pullulan as a substrate for the enzyme.

The procedure of Example 1 was repeated except that mammalian debranching enzyme was substituted for pullulanase in the reagent solution.

Inhibition of color formation in the samples containing body fluids from patients having CF was observed in comparison to the rate of color formation in samples containing body fluids from normal individuals. Controls for false positives were prepared in the same manner as in Example 1 by substituting maltose for the pullulan in the reagent solution.

EXAMPLE 3

This example illustrates the inhibition of pullulanase by CF ciliostatic factor using maltodextrin phosphorylase limit dextrin as a substrate.

A maltodextrin phosphorylase limit dextrin substrate solution is prepared by dissolving an excess amount, e.g., 2000 mg, of maltodextrin phosphorylase limit dextrin in the buffer of Example 1. The reagent solution is then prepared by adding the glucose-determining reagent as in Example 1.

Samples containing maltase, pullulanase and body fluid are prepared as in Example 1 above, except that when using maltodextrin phosphorylase limit dextrin as a substrate, the body fluids must be at least partially purified to remove endogenous amylases which can degrade the substrate.

The reaction is conducted and followed as in Example 1. Inhibition of the rate of color formation in samples containing body fluids from CF patients is observed when compared with the rate for samples containing body fluids from normal individuals. A confirmatory control for false positives is prepared as in Example 1 by substituting maltose for the maltodextrin phosphorylase limit dextrin in the reagent.

EXAMPLE 4

This example illustrates the inhibition of mammalian debranching enzyme by CF ciliostatic factor using maltodextrin phosphorylase limit dextrin as a substrate.

Example 3 was repeated except that mammalian debranching enzyme was substituted for the pullulanase used in Example 3.

Inhibition of color formation in the samples containing body fluids from patients having CF was observed in comparison with the rate of color formation in samples containing body fluids from normal individuals. Controls for false positives were prepared in the same manner as in Example 1 by substituting maltose for the pullulan in the reagent solution.

EXAMPLE 5

This example illustrates the inhibition of pullulanase by CF ciliostatic factor using purified preparations of CF ciliostatic factor.

CF ciliostatic factor was purified by affinity and chromatographic methods as described in published scientific literature (Impero, J. E., Pediatric Res. 12, 108-114 (1978). Control samples were prepared by sujecting body fluids from normal individuals to the same purificaton procedure. Aliquots (40 microliters) of the purified body fluids were pre-incubated with 20 microliters of pullulanase (2.9 units), 10 microliters of maltose (0.56 units), 80 microliters of a pH 6.6 buffer containing 10 mg/ml of pullulan in a total reaction volume of 1150 microliters. The samples were incubated at 30° C for 15 minutes. The reaction was stopped by placing the reaction tubes into a thermal block at a temperature of 100° C for one minute. The samples were then cooled and glucose production was monitored by adding 1 ml of hexokinase-based glucose reagent, and the absorbance change was determined as described in Example 1. Those samples containing CF ciliostatic factor exhibited decreased production of glucose as compared with the samples containing body fluid from normal individuals.

EXAMPLE 6

This example illustrates the inhibition of mammalian debranching enzyme by CF ciliostatic factor using purified preparations of CF ciliostatic factor.

Cystic fibrosis ciliostatic factor was purified by conventional affinity and chromatographic methods as in Example 5. Control samples were prepared by subjecting body fluid from individuals thought to be normal to the same purification procedure. Aliquots (40 microliters) of each sample and control sample were preincubated with 20 microliters of a solution of mammalian debranching enzyme containing 10 microliters of maltase (0.56 units). The preincubation solution was then added to a solution of 80 microliters of maltodextrin phosphorylase limit dextrin substrate in a pH 6.6 buffer. The samples were incubated at 30° C. for 15 minutes and the reaction was then stopped by placing the reaction tubes in a thermal block at 100° C. for one minute. The samples were then cooled to room temperature and the glucose produced was determined by adding 1 ml of a hexokinase-based glucose reagent as described in Example 1.

The samples containing CF ciliostatic factor exhibited inhibited glucose formation as compared with the control samples.

EXAMPLE 7

This example illustrates the inhibition of mammalian debranching enzyme by CF ciliostatic factor using purified preparations of CF ciliostatic factor and pullulan as a substrate.

Example 6 was repeated except that pullulan was used in place of the maltodextrin phosphorylase limit dextrin as the enzyme substrate.

The samples containing CF ciliostatic factor exhibited inhibited glucose forxation as compared with the control samples.

EXAMPLE 8

This example illustrates the inhibition of pullulanase by CF ciliostatic factor using purified preparations of CF ciliostatic factor.

Example 6 was repeated except that pullulanase was used in place of the mammalian debranching enzyme.

The samples containing CF ciliostatic factor exhibited inhibited glucose formation as compared with the control samples.

The invention having now been fully described, it will be apparent to those skilled in the art that many modifications and variations may be made therein without departing from the spirit and scope of the invention.

I claim:

1. A method for detecting cystic fibrosis ciliostatic factor in mammalian body fluid comprising contacting an enzyme whose activity is inhibited by cystic fibrosis ciliostatic factor with an amylase-resistant polysaccharide substrate capable of undergoing a chemical reaction catalyzed by said enzyme, and a mammalian body fluid which may contain said cystic fibrosis ciliostatic factor, said amylase-resistant polysaccharide being substantially resistant to reactions catalyzed by enzymes in said body fluid, whereby said substrate is converted to a product by said enzyme at a measurable rate, and comparing said rate of amylase-resistant polysaccharide conversion to said product with the rate of amylase-resistant polysaccharide conversion to said product by said enzyme in the absence of cystic fibrosis ciliostatic factor, determining the presence of cystic fibrosis ciliostatic factor from the comparison of rates, whereby the presence of said cystic fibrosis ciliostatic factor in said body fluid is detected by a decreased rate of substrate conversion to said product relative to the rate of conversion to said product in the absence of said cystic fibrosis ciliostatic factor.

2. The method of claim 1 wherein said enzyme is pullulanase.

3. The method of claim 1 wherein said enzyme is mammalian debranching enzyme.

4. The method of claim 1 wherein said amylase-resistant polysaccharide substrate is pullulan.

5. The method of claim 1 wherein said amylase resistant polysaccharide substrate is the product of an alpha-amylase digestion of maltodextrin phosphorylase limit dextrin.

6. The method of claim 5 wherein said polysaccharide has the formula

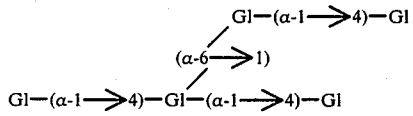

wherein G1 signifies an anhydroglucose residue and the numbers in parentheses indicate the locations of the bonds between the residues.

7. A reagent composition for determining cystic fibrosis ciliostatic factor in crude mammalian body fluid comprising a first composition comprising an enzyme whose activity is inhibited by cystic fibrosis ciliostatic factor, a second composition comprising an amylase-resistant polysaccharide substrate for said enzyme, capable of undergoing a chemical reaction catalyzed by said enzyme, said amylase-resistant polysaccharide being substantially resistant to reactions catalyzed by other enzymes in said body fluid.

8. The reagent composition of claim 7 wherein said enzyme is pullulanase.

9. The reagent composition of claim 7 wherein said enzyme is mammalian debranching enzyme.

10. The reagent composition of claim 7 wherein said amylase-resistant polysaccharide substrate is pullulan.

11. The reagent composition of claim 7 wherein said first composition also contains maltase.

12. The reagent composition of claim 7 wherein said second composition also contains a glucose-detecting reagent.

13. A kit for determining cystic fibrosis ciliostatic factor in a crude mammalian body fluid comprising a first container containing an enzyme whose activity is inhibited by cystic fibrosis ciliostatic factor, and a second container containing an amylase-resistant polysaccharide substrate for said enzyme, capable of undergoing a chemical reaction catalyzed by said enzyme, said amylase-resistant polysaccharide being substantially resistant to reactions catalyzed by other enzymes in said body fluid.

14. The kit of claim 13 wherein said enzyme is pullulanase.

15. The kit of claim 13 wherein said enzyme is mammalian debranching enzyme.

16. The kit of claim 13 wherein said amylase-resistant polysaccharide is pullulan.

17. The kit of claim 15 wherein said first container also contains maltase.

18. The kit of claim 13 wherein said second container also contains a glucose-detecting reagent.

19. The kit of claim 13 additionally comprising a container containing maltose.

20. The kit of claim 13 additionally comprising a container containing an enzyme inhibitor selected from the group consisting of nojirimycin and 1 deoxynojirimycin.

* * * * *